US010420695B2

United States Patent
Lee (10) Patent No.: US 10,420,695 B2
(45) Date of Patent: Sep. 24, 2019

(54) EXOSKELETON APPARATUS DRIVEN BY PNEUMATIC ARTIFICIAL MUSCLE WITH FUNCTIONS OF UPPER LIMB ASSIST AND REHABILITATION TRAINING

(71) Applicant: LUNGHWA UNIVERSITY OF SCIENCE AND TECHNOLOGY, Taoyuan (TW)

(72) Inventor: Lian-Wang Lee, Taoyuan (TW)

(73) Assignee: Lunghwa University of Science and Technology, Taoyuan (TW)

( * ) Notice: Subject to any disclaimer, the term of this patent is extended or adjusted under 35 U.S.C. 154(b) by 296 days.

(21) Appl. No.: 15/485,486

(22) Filed: Apr. 12, 2017

(65) Prior Publication Data

US 2017/0296418 A1  Oct. 19, 2017

(30) Foreign Application Priority Data

Apr. 15, 2016 (TW) .............................. 105111780 A (51) Int. Cl.
| | |
|---|---|
| A61H 1/02 | (2006.01) |
| B25J 9/00 | (2006.01) |
| A61F 5/01 | (2006.01) |
| B25J 9/10 | (2006.01) |

(52) U.S. Cl.
CPC ......... *A61H 1/0281* (2013.01); *A61H 1/0277* (2013.01); *A61F 2005/0155* (2013.01); *A61H 1/0274* (2013.01); *A61H 2201/1238* (2013.01); *A61H 2201/165* (2013.01); *B25J 9/0006* (2013.01); *B25J 9/1075* (2013.01)

(58) Field of Classification Search
CPC ... A61H 1/0277; A61H 1/0281; A61H 1/0274
See application file for complete search history.

(56) References Cited

U.S. PATENT DOCUMENTS

| 7,066,896 B1* | 6/2006 | Kiselik | .................... A61H 1/02 601/33 |
|---|---|---|---|
| 2006/0161220 A1* | 7/2006 | Kobayashi | ............ A61F 5/0102 607/49 |
| 2010/0063601 A1* | 3/2010 | Sankai | ................. A61H 1/0237 623/25 |

(Continued)

FOREIGN PATENT DOCUMENTS

CN           101564841 A  * 10/2009

*Primary Examiner* — David H Willse
*Assistant Examiner* — Javier G Blanco
(74) *Attorney, Agent, or Firm* — Rosenberg, Klein & Lee (57) ABSTRACT

An exoskeleton apparatus driven by a pneumatic artificial muscle with functions of upper limb assist and rehabilitation training includes an upper limb frame, a shoulder joint mechanism, and an elbow joint mechanism which are driven by utilizing a processing unit, a first angle sensing unit, a second angle sensing unit, a first proportional pressure valve, a pressure sensing unit and a pneumatic muscle device. The exoskeleton apparatus can be independently used as an upper limb exoskeleton assistive device or can be combined to form an upper limb exoskeleton rehabilitation training system to simulate the upper limb movements in daily life through the upper limb frame to assist with the movements of the wearer's upper limbs, accomplishing the rehabilitation training of each upper and lower arm joint and neurological function.

8 Claims, 5 Drawing Sheets

(56) References Cited

U.S. PATENT DOCUMENTS

| | | | |
|---|---|---|---|
| 2014/0212243 A1* | 7/2014 | Yagi | A61H 3/00 |
| | | | 414/2 |
| 2016/0058647 A1* | 3/2016 | Maddry | B25J 9/0006 |
| | | | 623/26 |
| 2016/0206497 A1* | 7/2016 | Deshpande | A61H 1/02 |

* cited by examiner

EXOSKELETON APPARATUS DRIVEN BY PNEUMATIC ARTIFICIAL MUSCLE WITH FUNCTIONS OF UPPER LIMB ASSIST AND REHABILITATION TRAINING

FIELD OF THE INVENTION

The present invention relates to an exoskeleton apparatus driven by a pneumatic artificial muscle with functions of upper limb assist and rehabilitation training, and more particularly to an exoskeleton apparatus which can simulate the movements of upper limbs in daily life through an upper arm mechanism and a lower arm mechanism to assist with the movements of the wearer's upper limbs, accomplishing the rehabilitation training of each upper and lower arm joint and neurological function.

BACKGROUND OF THE INVENTION

Human upper limb motion is one of the most important exercise limbs that affect the general public's ability in daily life, which is also the most vulnerable part of the limbs. With the improvement and development of science and technology, the number of domestic transport vehicles increases rapidly, and the number of upper limb injuries caused by traffic accidents grows increasingly. Simultaneously, our country and the most countries in the world are entering the aging society. Currently, the population aging rate of our country is ranked second in the world, next only to Japan. Among that, the ratio of population over 65 years old is 10.7% in our country in 2010. The Council for Economic Planning and Development (abbreviated to CEPD, on 22 Jan. 2014, CEPD was merged with Research, Development and Evaluation Commission to form the National Development Council) estimates that it will multiply to 20% in 2025. For elderly people, there are many people with various degrees of degradation or weakening in upper limb ability. With the improvement of living standards, the number of upper limb hemiplegia caused by the heart and cerebrovascular disease is increasing. Cerebral stroke is one of the common diseases, according to Ministry of Health and Welfare's (abbreviated to MOHW) statistics. The number of deaths due to cerebral strokes is about 13,000 per year, which is the second among the top ten leading causes of death in our country. About 17,000 people per year are lead to disability of daily life due to cerebral strokes, which is the most important reason of physical disability in Taiwanese adults, but even one of the top three of using health insurance resources. Therefore, it causes a heavy burden to the family and society and brings patients with great mental and physical torture.

With the increasing maturity of robotic technology, robots have a clear advantage in providing long-term repeatability and quantitative movement. In addition, the robotic technology has been widely used in various fields. A rehabilitation training system is an innovated application of the robot technology in the medical field, and it is also one of topic issues of robot research in domestic and overseas.

Compared to the traditional rehabilitation training methods, it is obvious that the rehabilitation training system has a certain degree of superiority. It can work continuously for a long time and develop different training intensity according to different patients. This not only can reduce the workloads of physical therapists but also through the quantitative exercise to stimulate, detect and evaluate the accumulation of a large number of clinical rehabilitation data, and helps researchers or physical therapists to further understand the relevance of various training data and rehabilitation effects, providing patients with a more scientific rehabilitation training model.

However, as to the existing upper limb exoskeleton assist and rehabilitation training system, the training actions provided by the system are comparatively simple, which are generally limited to rectilinear motions or curvilinear motions of the horizontal plane. The system cannot provide a wide range of space movement. Thus, it cannot give patients more correct exercise sensory stimulation in the early rehabilitation. Besides, the mechanical arm and the patient's limbs are connected through a point to exercise, which cannot provide sufficient strength and flexibility and also has worse pliability and safety. As a result, the user's limbs may be damaged easily by external forces during training. Meanwhile, due to the complex structure of the motor drive system, it is not easy for the mechanism to be light in weight when increasing the degree of freedom of the exoskeleton system. Furthermore, the drive mode is mainly done with the motor. The system has the drawbacks of complex configuration, high rigidity, and lack of pliability. The training modes are few. The most basic requirement of the rehabilitation training is to enable patients to restore the ability of simple daily life. But some of these actions are different from the daily functional actions, which are not very helpful to patients to restore the ability of daily life. Thus, this kind of assistive device and rehabilitation training system is hard to achieve a good rehabilitation effect.

Accordingly, the inventor of the present invention has devoted himself based on his many years of practical experiences to solve these problems.

SUMMARY OF THE INVENTION

In view of the shortcomings of the prior art, the primary object of the present invention is to provide an exoskeleton apparatus driven by a pneumatic artificial muscle with functions of upper limb assist and rehabilitation training. As to the conventional upper limb exoskeleton assist and rehabilitation training system, the training actions provided by the system are comparatively simple, which are generally limited to rectilinear motions or curvilinear motions of the horizontal plane. The system cannot provide a wide range of space movement. Thus, it cannot give patients more correct exercise sensory stimulation in the early rehabilitation. Besides, the mechanical arm and the patient's limbs are connected through a point to exercise, which cannot provide sufficient strength and flexibility and also has worse pliability and safety. As a result, the user's limbs may be damaged easily by external forces during training.

In order to achieve the aforesaid object, the exoskeleton apparatus driven by a pneumatic artificial muscle with functions of upper limb assist and rehabilitation training of the present invention comprises a main body. The main body includes an upper limb frame. The upper limb frame is provided with a shoulder joint mechanism. The shoulder joint mechanism is coupled with a first angle sensing unit. The shoulder joint mechanism is provided with an upper arm mechanism. One side of the upper arm mechanism, opposite to the shoulder joint mechanism, is provided with an elbow joint mechanism. The elbow joint mechanism is coupled with a second angle sensing unit. One side of the elbow joint mechanism, opposite to the upper arm mechanism, is provided with a lower arm mechanism. One side of the lower arm mechanism, opposite to the elbow joint mechanism, is provided with a pressure sensing unit. The upper limb frame is provided with a pneumatic muscle device relative to the shoulder joint mechanism. The pneumatic muscle device is coupled with a processing unit and a first proportional pressure valve. The processing unit is coupled with the first angle sensing unit, and the first proportional pressure valve. The shoulder joint mechanism is connected with the pneumatic muscle device through a transmission device.

Preferably, the upper arm mechanism is provided with a pressure measurement unit. The pressure measurement unit is coupled with the processing unit.

Preferably, the processing unit is provided with a set value. When an applied force is greater than the set value, the processing unit commands the pneumatic muscle device to actuate.

Preferably, one side of the main body, opposite to the pneumatic muscle device, is provided with a retaining device.

Preferably, an inner side of the upper limb frame is provided with an adjustment device.

Preferably, one side of the main body, opposite to the shoulder joint mechanism, is provided with a wrist joint mechanism. The wrist joint mechanism is coupled with a third angle sensing unit. The third angle sensing unit is coupled with the processing unit.

Preferably, a bottom end of the main body is further provided with a base. The base includes a pneumatic actuator. The pneumatic actuator is coupled with a second proportional pressure valve. The second proportional pressure valve is coupled with the processing unit.

Preferably, the main body is covered with a housing.

Preferably, the upper limb frame is made of aluminum alloy.

Preferably, the transmission device is a steel wire.

It is obvious that the present invention has the following advantages and beneficial effects.

The present invention uses flexibility and low cost of the pneumatic muscle device, which can be independently used as an upper limb exoskeleton assistive device or can be combined to form an upper limb exoskeleton rehabilitation training system. The exoskeleton apparatus can assist with the movements of upper limbs for an able-bodied person or a person with weak muscles. Besides, it is able to perform an autonomous control based on the information of the first angle sensing unit, the second angle sensing unit, the third angle sensing unit, the pressure measurement unit, and the pressure sensing unit so as to help aged people and those with weak limbs to improve their ability and living independently. The exoskeleton apparatus can be used at home for hemiplegic patients to simulate the upper limb movements in daily life through the upper limb frame to assist with the movements of the wearer's upper limbs, accomplishing the rehabilitation training of each upper and lower arm joint and neurological function.

The present invention can be used for different wearers who may have different heights, different affected sides, and different degrees of damage. The postures of the upper arm mechanism and the lower arm mechanism of the upper limb frame are adjustable, including outward extension, inward contraction, bending-stretching motions of the shoulder, bending-stretching motions of the wrist, and bending-stretching motions and the internal and external rotations of the wrist, so to train the motions of the daily life for the wearer to train the ability of the left and right arms or the autonomy rehabilitation of the affected side by the healthy side of the patient, thereby achieving the purpose of upper limb rehabilitation training for the patients.

DETAILED DESCRIPTION OF THE PREFERRED EMBODIMENTS

Embodiments of the present invention will now be described, by way of example only, with reference to the accompanying drawings.

As shown in FIG. 1 to FIG. 4, an exoskeleton apparatus driven by a pneumatic artificial muscle with functions of upper limb assist and rehabilitation training of the present invention comprises a main body 1. The main body 1 includes an upper limb frame 11. In an embodiment, the upper limb frame 11 is made of an aluminum alloy material to reduce the weight of the apparatus. The upper limb frame 11 is provided with a shoulder joint mechanism 12. The shoulder joint mechanism 12 is coupled with a first angle sensing unit 121. The shoulder joint mechanism 12 is provided with an upper arm mechanism 13. In an embodiment, the upper arm mechanism 13 is provided with a pressure measurement unit (not shown). In an embodiment, the pressure measurement unit is a film pressure measurement unit. In another embodiment, the upper limb frame 11 and the upper arm mechanism 13 are adjustable in length according to the wearer's shoulder width and the upper arm. One side of the upper arm mechanism 13, opposite to the shoulder joint mechanism 12, is provided with an elbow joint mechanism 14. The elbow joint mechanism 14 is coupled with a second angle sensing unit 141. One side of the elbow joint mechanism 14, opposite to the upper arm mechanism 13, is provided with a lower arm mechanism 15. One side of the lower arm mechanism 15, opposite to the elbow joint mechanism 14, is provided with a pressure sensing unit 151.

The upper limb frame 11 is provided with a pneumatic muscle device 2 relative to the shoulder joint mechanism 12. The pneumatic muscle device 2 is coupled with a processing unit 21 and a first proportional pressure valve 22. The processing unit 21 is coupled with the first angle sensing unit 121, the second angle sensing unit 141, the pressure measurement unit, and the first proportional pressure valve 22. The processing unit 21 is provided with a set value F. When a force applied by the wearer is greater than the set value F, the processing unit 21 commands the pneumatic muscle device 2 to actuate. The shoulder joint mechanism 12 is connected with the pneumatic muscle device 2 through a transmission device 23. In an embodiment, the transmission device 23 is a steel wire. One end of the transmission device 23 is fixed to the corresponding shoulder joint mechanism 12, and another end of the transmission device 23 is connected to the corresponding pneumatic muscle device 2 via a hanging ring (not shown in the drawings).

One side of the main body 1, opposite to the pneumatic muscle device 2, is provided with a retaining device 16 which facilitates the wearer to wear and secure it to his/her back.

An inner side of the upper limb frame 11 is provided with an adjustment device 17 for the wearer to secure the upper and lower arms to the upper arm mechanism 13 and the lower arm mechanism 15, respectively.

Figure 1:
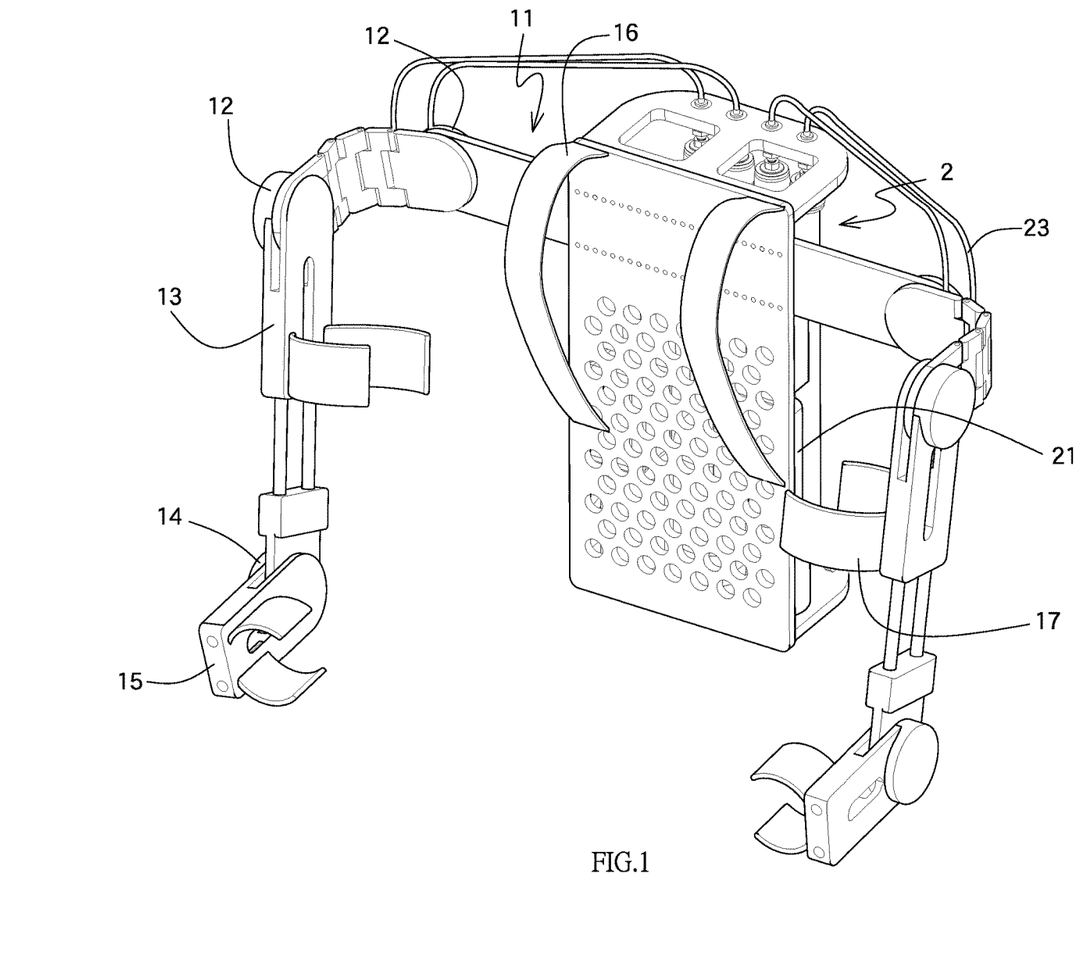
FIG. 1 is a front perspective view of the present invention.
Figure 2:
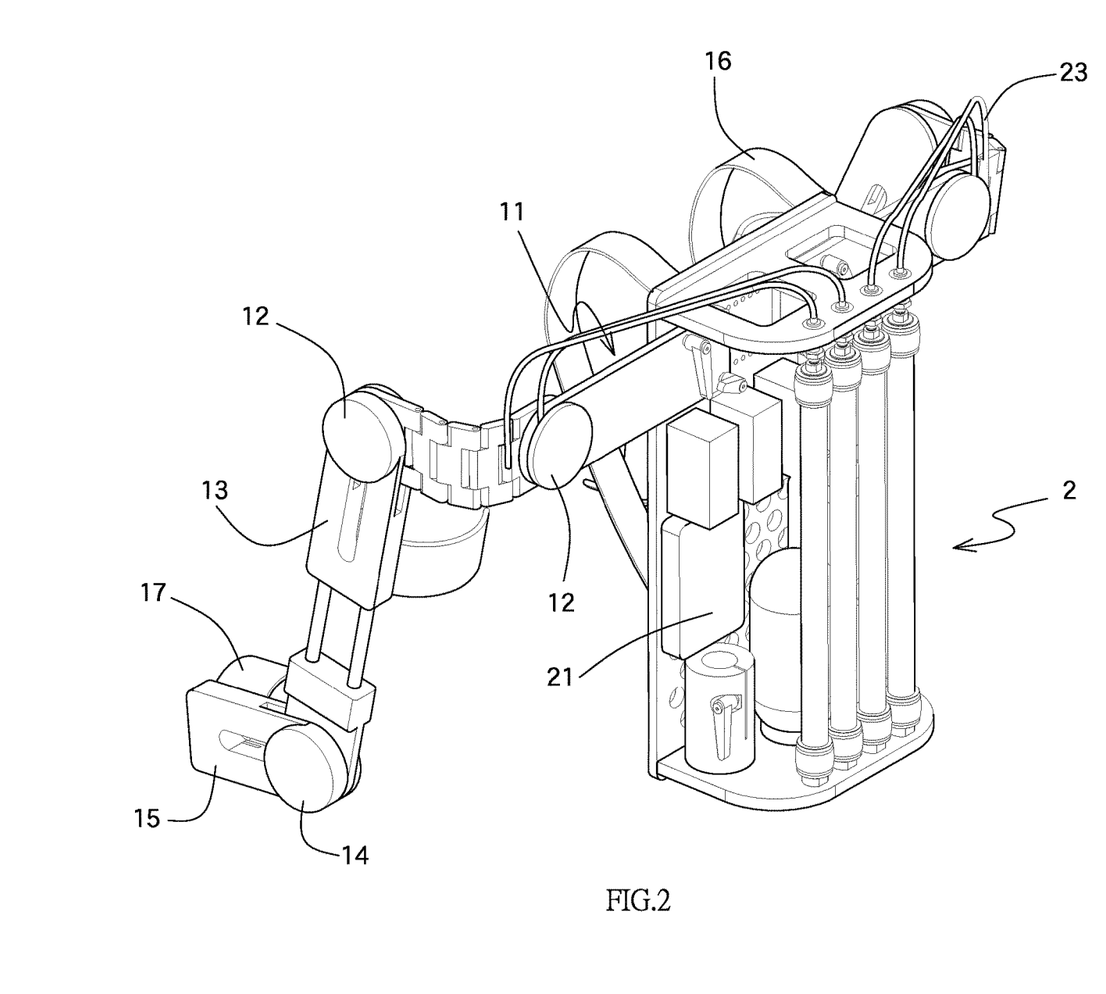
FIG. 2 is a rear perspective view of the present invention.
Figure 3:
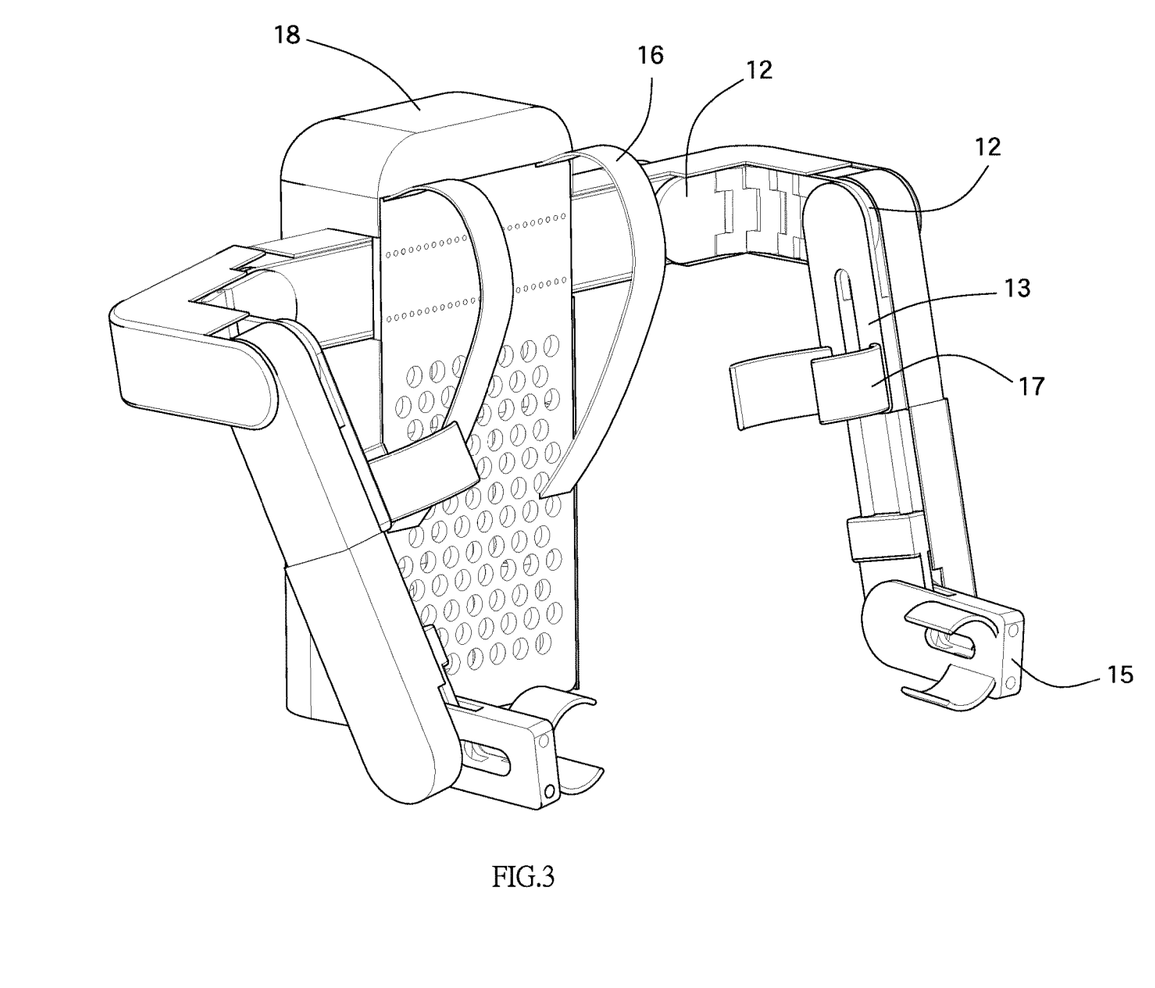
FIG. 3 is a perspective view of the present invention covered with a housing.
Figure 4:
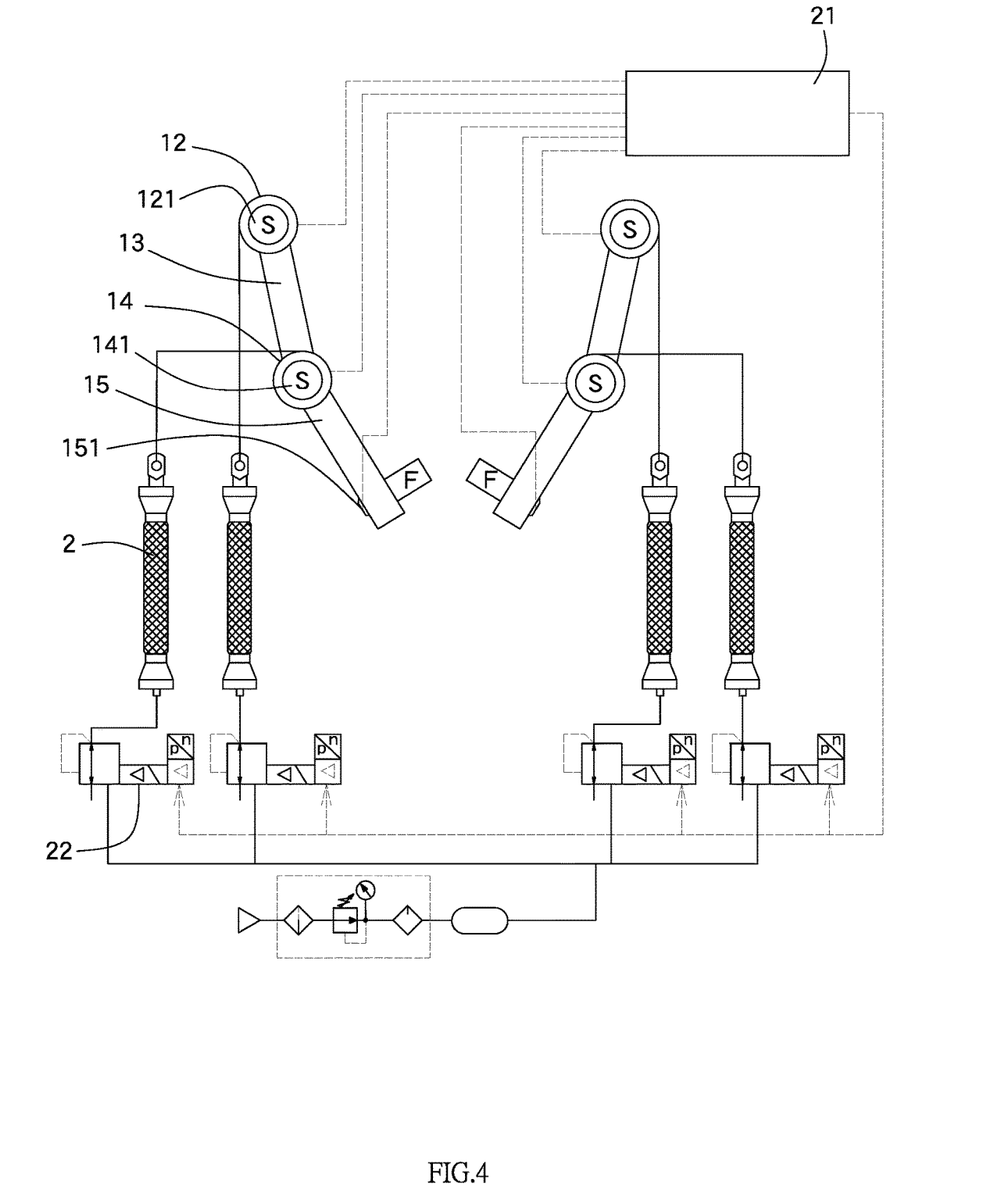
FIG. 4 is a structural schematic view of the present invention.

The main body 1 is covered with a housing 18, so that the upper limb frame 11, the pneumatic muscle device 2, and the transmission device 23 are received in the housing 18.

During the process of lifting a heavy article, the upper limb is mainly subjected to the torque of the shoulder and the elbow joints. Therefore, the present invention mainly aims at the two degrees of freedom of bending and stretching motions of the shoulder and elbow joints. The other two degrees of freedom (for example, the inward contraction and outward extension, internal and external rotation of the shoulder joint) are driven by the wearer's motion. The primary object of the present invention is to improve the ability of the upper limbs of the wearer. Thus, a film pressure measurement unit is used to measure the pressure between the upper and lower arms and the upper limb frame 11. When lifting a heavy article, the upper limb frame 11 can assist the wearer in lifting the heavy article in a labor-saving manner.

Thereby, when the wearer wears the exoskeleton apparatus, under the premise that the normal motion of the upper limb is not affected and that there is no need for the help of the pneumatic muscle device 2, the range of the freedom of the major motion of the upper limb frame 11 needs to be matched with the upper and lower arms of the wearer. That is, when the force is less than the set value F, it is determined that the wearer is ready to release the heavy article, and the pneumatic muscle device 2 is maintained in a state of pressure keeping, namely, not inflated or deflated.

When it is necessary for the help of the pneumatic muscle device 2, the operating mode is that the processing unit 21 continuously detects the force between the upper arm of the wearer and the upper arm mechanism 13. When the heavy article is lifted, the processing unit 21 drives the pneumatic muscle device 2 to inflate and deflate to output a reverse torque. The tension is transmitted to the shoulder joint mechanism 12 by the transmission device 23, thereby generating an assistive torque to maintain the force between the man and the machine within a predetermined range, so that a relatively small force is applied by the wearer, thereby reducing the burden of the upper limb of the wearer to lift the heavy article so as to achieve the assistive effect for lifting the heavy article. The movement locus of the system is controlled by the wearer. The amount of the assistive force outputted from the upper limb frame 11 is determined by the processing unit 21.

In addition, each of the shoulder joint mechanism 12 and the elbow joint mechanism 14 of the present invention is driven by one pneumatic muscle device 2. The pneumatic muscle device 2 controls the pressure output through the first proportional pressure valve 22. Compared to the pull-type joint drive, the single pneumatic muscle drive reduces the amount of the pneumatic muscle devices 2 and the first proportional pressure valves 22. Further, since the return of the joint angle is brought by the upper limb, the upper limb frame 11 of the present invention assists the wearer in lifting the heavy article. The cost is relatively low, and the control is relatively simple. The transmission of the assistive force adopts the traction of a steel wire. The pneumatic muscle device 2 is mounted to one side of the upper body frame 11 opposite the retaining device 16, so that the upper arm mechanism 13 is more compact. Therefore, the present invention collects the data based on the operating range and the speed of the assistive force provided by the upper arm mechanism 13 and the lower arm mechanism 15, the comfort of the limiting position, the safety and the stability of the movement.

Further, the upper limb frame 11 is mainly composed of the shoulder joint mechanism 12, the elbow joint mechanism 14, the upper arm mechanism 13, and the lower arm mechanism 15. In an embodiment, the present invention utilizes the D-H coordinate conversion method to analyze the end space pose of the upper limb frame 11, thereby obtaining the pose equation. Because the primary object of the present invention mainly is to assist with the two degrees of freedom of bending and stretching motions of the shoulder and the elbow joints, the other two degrees of freedom only follow the wearer's motion. Thus, in an embodiment, the present invention employs a Lagrange method, which establishes a generalized force equation for input and output through the Lagrange function constituted by the kinetic energy and the potential energy of the system. For the coordination, stability and safety of the man-machine and the flexibility of the distal locus, the angles of the shoulder joint mechanism 12 and the elbow joint mechanism 14 are required to reach the desired position and attitude stably and smoothly under a certain load. That is, when the wearer feels laborious to lift the heavy article, the processing unit 21 commands the upper limb frame 11 to increase the assistive force so that the wearer may feel lighter and more comfortable during the process of lifting the heavy article.

Figure 5:
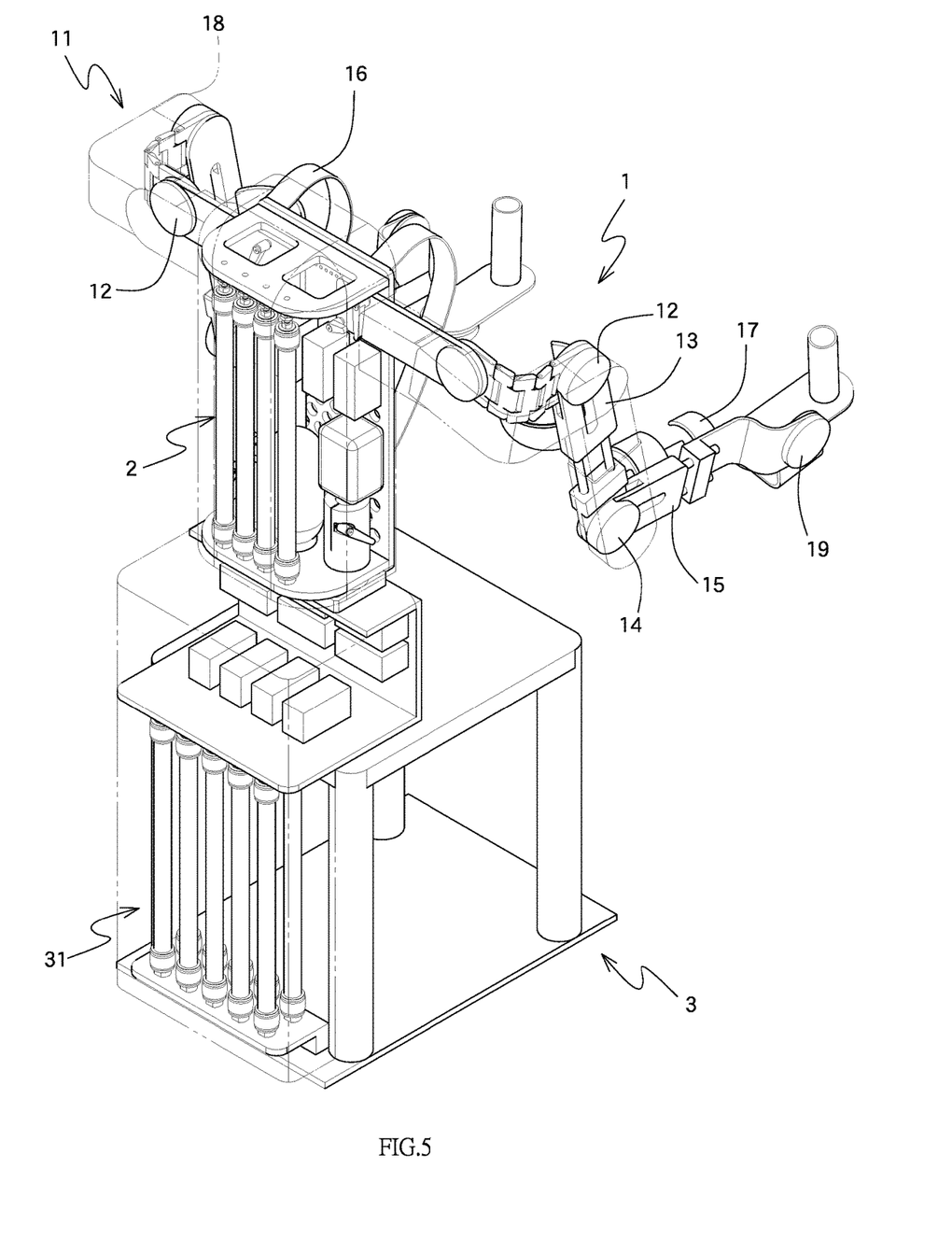
FIG. 5 is a perspective view of the present invention mounted to a base.

As shown in FIG. 5, in another embodiment of the present invention, a bottom end of the main body 1 is further provided with a base 3. The base 3 includes a pneumatic actuator 31. The pneumatic actuator 31 is coupled with a second proportional pressure valve (not shown in the drawings). The second proportional pressure valve is coupled with the processing unit 21. In an embodiment, the base 3 is adjustable in height. One side of the main body 1, opposite to the shoulder joint mechanism 12, is provided with a wrist joint mechanism 19. The wrist joint mechanism 19 is coupled with a third angle sensing unit (not shown in the drawings). The third angle sensing unit is coupled with the processing unit 21. Thus, the present invention can be used for different wearers who may have different heights, different affected sides, and different degrees of damage. The postures of the upper arm mechanism 13, the lower arm mechanism 15 of the upper limb frame 11 are adjustable, including outward extension, inward contraction, bending-stretching motions of the shoulder, bending-stretching motions of the wrist, and bending-stretching motions and the internal and external rotations of the wrist, so to train the motions of the daily life for the wearer to train the ability of the left and right arms or the autonomy rehabilitation of the affected side by the healthy side of the patient, thereby achieving the purpose of upper limb rehabilitation training for the patients.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. An exoskeleton apparatus driven by a pneumatic artificial muscle with functions of upper limb assist and rehabilitation training, comprising:

a main body, the main body including an upper limb frame, the upper limb frame being provided with a shoulder joint mechanism, the shoulder joint mechanism being coupled with a first angle sensing unit, the shoulder joint mechanism being provided with an upper arm mechanism, the upper arm mechanism being provided with a pressure measurement unit, one side of the upper arm mechanism, opposite to the shoulder joint mechanism, being provided with an elbow joint mechanism, the elbow joint mechanism being coupled with a second angle sensing unit, one side of the elbow joint mechanism, opposite to the upper arm mechanism, being provided with a lower arm mechanism, one side of the lower arm mechanism, opposite to the elbow joint mechanism, being provided with a pressure sensing unit, the upper limb frame being provided with a pneumatic muscle device relative to the shoulder joint mechanism, the pneumatic muscle device being coupled with a processing unit and a first proportional pressure valve, the processing unit being coupled with the first angle sensing unit, the second angle sensing unit, the pressure measurement unit, the pressure sensing unit, and the first proportional pressure valve, the shoulder joint mechanism being connected with the pneumatic muscle device through a transmission device;

the processing unit being provided with a set value, the pressure sensing unit being adapted to detect a force, a value of the force detected by the pressure sensing unit being sent to the processing unit for making an analysis; wherein when the value of the force is greater than the set value, the processing unit commands the pneumatic muscle device to actuate; when the force is less than the set value, the pneumatic muscle device is maintained in a state of pressure keeping.

2. The exoskeleton apparatus as claimed in claim 1, wherein one side of the main body, opposite to the pneumatic muscle device, is provided with a retaining device.

3. The exoskeleton apparatus as claimed in claim 1, wherein an inner side of the upper limb frame is provided with an adjustment device.

4. The exoskeleton apparatus as claimed in claim 1, wherein one side of the main body, opposite to the shoulder joint mechanism, is provided with a wrist joint mechanism, the wrist joint mechanism is coupled with a third angle sensing unit, and the third angle sensing unit is coupled with the processing unit.

5. The exoskeleton apparatus as claimed in claim 1, wherein a bottom end of the main body is further provided with a base, the base includes a pneumatic actuator, the pneumatic actuator is coupled with a second proportional pressure valve, and the second proportional pressure valve is coupled with the processing unit.

6. The exoskeleton apparatus as claimed in claim 1, wherein the main body is covered with a housing.

7. The exoskeleton apparatus as claimed in claim 1, wherein the upper limb frame is made of aluminum alloy.

8. The exoskeleton apparatus as claimed in claim 1, wherein the transmission device is a steel wire.

* * * * *